(12) United States Patent
LaVon et al.

(10) Patent No.: US 10,271,998 B2
(45) Date of Patent: Apr. 30, 2019

(54) SENSOR SYSTEMS COMPRISING ANTI-CHOKING FEATURES

(75) Inventors: Gary Dean LaVon, Liberty Township, OH (US); Vijay Rajagopalan, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 157 days.

(21) Appl. No.: 13/483,456

(22) Filed: May 30, 2012

(65) Prior Publication Data
US 2012/0310190 A1 Dec. 6, 2012

Related U.S. Application Data

(60) Provisional application No. 61/493,100, filed on Jun. 3, 2011, provisional application No. 61/493,092, filed
(Continued)

(51) Int. Cl.
A61F 13/42 (2006.01)
A61F 13/505 (2006.01)
(Continued)

(52) U.S. Cl.
CPC ............ *A61F 13/505* (2013.01); *A61F 13/42* (2013.01); *A61F 13/496* (2013.01); *A61F 13/514* (2013.01); *A61F 13/51401* (2013.01); *A61F 13/51474* (2013.01); *A61F 13/58* (2013.01); *A61F 13/625* (2013.01); *A61F 13/80* (2013.01); *A61F 13/84* (2013.01); *G01N 27/048* (2013.01); *G01N 33/4875* (2013.01);
(Continued)

(58) Field of Classification Search
CPC ......... A61F 13/42; A61F 2013/421–2013/429; A61F 2013/424; A61F 2013/8473; A61F 2013/8476; A61F 2013/8479; A61F 2013/8482
USPC ........................................................ 604/361
See application file for complete search history.

(56) References Cited

U.S. PATENT DOCUMENTS 4,286,331 A 8/1981 Anderson
4,554,662 A 11/1985 Suzuki
(Continued)

FOREIGN PATENT DOCUMENTS

EP 0 149 880 A2 5/1984
EP 1 216 673 B1 10/2005
(Continued)

OTHER PUBLICATIONS

16 C.F.R. Part 1501 and 1500.50-53, Jan. 2001.*
(Continued)

*Primary Examiner* — Catharine L Anderson
(74) *Attorney, Agent, or Firm* — Richard L. Alexander

(57) ABSTRACT

A sensor system for detecting a property of or within an absorbent article may comprise an absorbent article and a sensor. The absorbent article may comprise a garment-facing layer and an absorbent assembly. The sensor may be disposed in or on the absorbent article. The sensor may be separable from the absorbent article. A portion of the sensor may have a first dimension and a second dimension, wherein the first dimension is at least 1 inch and the second dimension is at least 2 inches. The sensor may be configured to sense a change in condition within the absorbent article.

20 Claims, 11 Drawing Sheets

Related U.S. Application Data on Jun. 3, 2011, provisional application No. 61/493,095, filed on Jun. 3, 2011.

(51) Int. Cl.

| | |
|---|---|
| A61F 13/496 | (2006.01) |
| A61F 13/58 | (2006.01) |
| A61F 13/62 | (2006.01) |
| A61F 13/84 | (2006.01) |
| A61F 13/80 | (2006.01) |
| A61F 13/514 | (2006.01) |
| G01N 27/04 | (2006.01) |
| G01N 33/487 | (2006.01) |
| H02J 7/00 | (2006.01) |
| A61F 13/15 | (2006.01) |
| G01N 21/84 | (2006.01) |
| G01N 27/02 | (2006.01) |

(52) U.S. Cl.
CPC .......... *H02J 7/0027* (2013.01); *H02J 7/0045* (2013.01); *A61F 2013/1513* (2013.01); *A61F 2013/422* (2013.01); *A61F 2013/424* (2013.01); *A61F 2013/51441* (2013.01); *A61F 2013/8497* (2013.01); *G01N 21/84* (2013.01); *G01N 27/02* (2013.01)

(56) References Cited

U.S. PATENT DOCUMENTS

| | | | |
|---|---|---|---|
| 4,940,464 A | 7/1990 | Van Gompel et al. | |
| 5,264,830 A | 11/1993 | Kline et al. | |
| 5,469,145 A | 11/1995 | Johnson | |
| 5,709,222 A | 1/1998 | Davallou | |
| 6,093,869 A | 7/2000 | Roe et al. | |
| 6,203,496 B1 | 3/2001 | Gael et al. | |
| 6,617,488 B1 | 9/2003 | Springer et al. | |
| 6,645,190 B1 | 11/2003 | Olson et al. | |
| 7,002,054 B2 | 2/2006 | Allen et al. | |
| 7,049,969 B2 | 5/2006 | Tamai | |
| 7,174,774 B2 | 2/2007 | Pawar | |
| 7,250,547 B1 | 7/2007 | Hofmeister et al. | |
| 8,044,258 B2 | 10/2011 | Hietpas | |
| 8,053,625 B2 | 11/2011 | Nhan et al. | |
| 8,196,270 B2 | 6/2012 | Mandzsu | |
| 8,314,284 B1 | 11/2012 | Novello | |
| 8,350,694 B1 | 1/2013 | Trundle | |
| 8,546,639 B2 | 10/2013 | Wada et al. | |
| 8,785,716 B2 | 7/2014 | Schafer et al. | |
| 9,211,218 B2 | 12/2015 | Rinnert et al. | |
| 9,301,884 B2 | 4/2016 | Shah et al. | |
| 2003/0130637 A1 | 7/2003 | Intravartolo et al. | |
| 2004/0064114 A1 | 4/2004 | David | |
| 2004/0127867 A1 | 7/2004 | Odorzynski et al. | |
| 2004/0236302 A1 | 11/2004 | Wilhelm et al. | |
| 2004/0254549 A1* | 12/2004 | Olson et al. | 604/361 |
| 2005/0099294 A1 | 5/2005 | Bogner | |
| 2005/0137542 A1 | 6/2005 | Underhill et al. | |
| 2006/0264861 A1 | 11/2006 | Lavon | |
| 2007/0142797 A1* | 6/2007 | Long et al. | 604/361 |
| 2007/0156106 A1 | 7/2007 | Klofta | |
| 2007/0233027 A1* | 10/2007 | Roe et al. | 604/361 |
| 2007/0252710 A1 | 11/2007 | Long | |
| 2007/0252711 A1 | 11/2007 | Long et al. | |
| 2007/0252713 A1 | 11/2007 | Rondoni et al. | |
| 2008/0021428 A1 | 1/2008 | Klofta et al. | |
| 2008/0074274 A1* | 3/2008 | Hu | A61F 13/42 |
| | | | 340/573.5 |
| 2008/0082063 A1 | 4/2008 | Ales | |
| 2008/0147031 A1* | 6/2008 | Long et al. | 604/361 |
| 2008/0208155 A1 | 8/2008 | Lavon | |
| 2008/0234644 A1* | 9/2008 | Hansson et al. | 604/360 |
| 2008/0266123 A1 | 10/2008 | Ales | |
| 2008/0300559 A1 | 12/2008 | Gustafson | |
| 2009/0062756 A1* | 3/2009 | Long et al. | 604/361 |
| 2009/0124990 A1 | 5/2009 | Feldkamp et al. | |
| 2009/0326409 A1 | 12/2009 | Cohen et al. | |
| 2010/0013778 A1 | 1/2010 | Liu | |
| 2010/0160882 A1 | 6/2010 | Lowe | |
| 2010/0164733 A1* | 7/2010 | Ales et al. | 340/604 |
| 2010/0168702 A1 | 7/2010 | Ales et al. | |
| 2010/0241094 A1 | 9/2010 | Sherron | |
| 2011/0251038 A1 | 10/2011 | Lavon | |
| 2011/0298597 A1 | 12/2011 | Kaihori | |
| 2012/0061016 A1 | 3/2012 | Lavon | |
| 2012/0116337 A1 | 5/2012 | Ales | |
| 2012/0157947 A1* | 6/2012 | Nhan | A61F 13/42 |
| | | | 604/361 |
| 2012/0161960 A1* | 6/2012 | Cheng | A61F 13/42 |
| | | | 340/539.12 |
| 2012/0172824 A1 | 7/2012 | Khaknazarov | |
| 2012/0190956 A1 | 7/2012 | Connolly | |
| 2012/0206265 A1 | 8/2012 | Solazzo | |
| 2012/0225200 A1 | 9/2012 | Mandzsu | |
| 2012/0299721 A1 | 11/2012 | Jones | |
| 2012/0310190 A1 | 12/2012 | LaVon et al. | |
| 2013/0041334 A1 | 2/2013 | Prioleau | |
| 2013/0110063 A1 | 5/2013 | Abraham | |
| 2013/0261409 A1 | 10/2013 | Pathak | |
| 2015/0025347 A1 | 1/2015 | Song | |
| 2015/0042489 A1 | 2/2015 | LaVon et al. | |
| 2015/0112202 A1 | 4/2015 | Abir | |
| 2016/0078716 A1 | 3/2016 | Olafsson-Ranta et al. | |
| 2016/0080841 A1 | 3/2016 | Bergstrom et al. | |
| 2016/0113822 A1 | 4/2016 | Vartiainen et al. | |
| 2016/0134497 A1 | 5/2016 | Hermansson et al. | |
| 2016/0170776 A1 | 6/2016 | Bergstrom et al. | |
| 2016/0235603 A1 | 8/2016 | Ehrnsperger et al. | |
| 2016/0374868 A1 | 12/2016 | Ettrup Hansen | |

FOREIGN PATENT DOCUMENTS

| | | |
|---|---|---|
| EP | 1 542 635 | 4/2012 |
| EP | 1542635 B1 | 4/2012 |
| EP | 2 491 899 | 7/2014 |
| EP | 2491899 B1 | 7/2014 |
| JP | 09187431 A | 7/1997 |
| JP | 2002-022687 A | 1/2002 |
| JP | 2002/143199 A | 5/2002 |
| JP | 2003/190209 A | 7/2003 |
| JP | 2004/041697 | 2/2004 |
| JP | 2004/230135 A | 8/2004 |
| JP | 2006/296566 A | 11/2006 |
| WO | WO 1995-16746 | 6/1995 |
| WO | WO 1999-34841 | 7/1999 |
| WO | WO 2010-123364 A1 | 10/2010 |
| WO | WO 2010-123425 A1 | 10/2010 |
| WO | WO 2011-013874 A1 | 2/2011 |
| WO | WO 2012-084925 A1 | 6/2012 |
| WO | WO 2012-126507 A1 | 9/2012 |
| WO | WO 2012-166765 | 12/2012 |
| WO | WO 2013-003905 | 1/2013 |
| WO | WO2013-003905 | 1/2013 |
| WO | WO2013016765 A1 | 2/2013 |
| WO | WO 2013-061963 A1 | 5/2013 |
| WO | WO2013-091728 | 6/2013 |
| WO | WO2013-095226 | 6/2013 |
| WO | WO2013-095230 | 6/2013 |
| WO | WO2013091707 A1 | 6/2013 |
| WO | WO2013095222 A1 | 6/2013 |
| WO | WO2013095231 | 6/2013 |
| WO | WO2013-097899 | 7/2013 |
| WO | WO 2013-185419 | 12/2013 |
| WO | WO 2013-189284 A1 | 12/2013 |
| WO | WO2013181436 A1 | 12/2013 |
| WO | WO2014035302 A1 | 3/2014 |
| WO | WO2014035340 A1 | 3/2014 |
| WO | WO 2014-122169 A1 | 8/2014 |
| WO | WO 2014-137671 | 9/2014 |
| WO | WO2014-137671 | 9/2014 |
| WO | WO 2014-146693 | 9/2014 |
| WO | WO2014-146693 | 9/2014 |
| WO | WO2014-146694 | 9/2014 |

(56) References Cited

FOREIGN PATENT DOCUMENTS

| WO | WO 2014-146694 | 9/2014 |
|----|----|----|
| WO | WO 2014-148957 A1 | 9/2014 |
| WO | WO2014-177200 | 11/2014 |
| WO | WO2014-177203 | 11/2014 |
| WO | WO2014-177204 | 11/2014 |
| WO | WO2014-177205 | 11/2014 |
| WO | WO2014-178763 | 11/2014 |
| WO | WO 20141177200 | 11/2014 |
| WO | WO 20141177203 | 11/2014 |
| WO | WO 20141177204 | 11/2014 |
| WO | WO 20141177205 | 11/2014 |
| WO | WO 20141178763 | 11/2014 |
| WO | WO 2014-192978 A1 | 12/2014 |
| WO | WO 2015/003712 | 1/2015 |
| WO | WO2015-003712 | 1/2015 |
| WO | WO 2015/068124 | 5/2015 |
| WO | WO2015-068124 | 5/2015 |
| WO | WO2015-102084 | 7/2015 |
| WO | WO 2015-102084 A1 | 7/2015 |
| WO | WO 2015-102085 A1 | 7/2015 |
| WO | WO2015102085 | 7/2015 |

OTHER PUBLICATIONS

PCT International Search Report, PCT/US2012/039940 dated May 30, 2012.
PCT International Search Report and Written Opinion, PCT/US2012/039943 dated Aug. 23, 2012.
All Office Actions and Responses, U.S. Appl. No. 13/483,463.
Non-Final Rejection for U.S. Appl. No. 13/483,463 dated May 21, 2014.
Amendment for U.S. Appl. No. 13/483,463 dated Aug. 21, 2014.
All Office Actions and Responses, U.S. Appl. No. 14/455,088.
All Office Actions and Responses, U.S. Appl. No. 13/483,456.
All Office Actions, U.S. Appl. No. 14/455,088.
All Office Actions, U.S. Appl. No. 15/497,367.
All Office Actions, U.S. Appl. No. 15/497,541.
All Office Actions, U.S. Appl. No. 15/497,574.
All Office Actions, U.S. Appl. No. 15/497,641.
All Office Actions, U.S. Appl. No. 15/497,674.
All Office Actions, U.S. Appl. No. 15/497,735.
All Office Actions, U.S. Appl. No. 15/497,823.
All Office Actions, U.S. Appl. No. 15/653,821.
All Office Actions, U.S. Appl. No. 15/705,996.
All Office Actions, U.S. Appl. No. 15/916,827.
All Office Actions, U.S. Appl. No. 15/916,854.
All Office Actions, U.S. Appl. No. 15/879,971.
All Office Actions, U.S. Appl. No. 13/483,463.
All Office Actions, U.S. Appl. No. 15/656,217.
All Office Actions, U.S. Appl. No. 15/134,035.

* cited by examiner

SENSOR SYSTEMS COMPRISING ANTI-CHOKING FEATURES

CROSS REFERENCE TO RELATED APPLICATION

This application claims the benefit of U.S. Provisional Application Nos. 61/493,092, 61/493,095, and 61/493,100, each filed on Jun. 3, 2011, and each of which are herein incorporated by reference in their entirety.

FIELD

In general, embodiments of the present disclosure relate to sensors for use with absorbent articles. In particular, embodiments of the present disclosure relate to sensors designed to lower the potential for accidental choking.

BACKGROUND OF INVENTION

The art discloses many different types of sensors that are integral with an absorbent article (e.g., placed internal of the garment-facing layer or fixed to interior or exterior surfaces of the garment-facing layer). One of the problems with designs having an internal sensor is that most are throw away sensors, i.e. the sensor is a single-use design disposed within the absorbent article primarily because it is undesirable to reuse them once they become contaminated with fecal waste and urine. Such an approach can be expensive given the need to incorporate a sensor into every absorbent article, e.g. a diaper. In addition, products that rely on an electrical circuit as the means for indication on the inside of the product can also expose the wearer to low voltage electrical current.

Alternatively, the sensor may be placed external of the garment-facing layer, but still integral with the absorbent article. One of the problems with a sensor fixed to the external surface of the garment-facing layer is creating a means for locating the sensor appropriately and then holding or attaching the sensor to the garment-facing layer.

Another problem with a sensor fixed to the external surface of the garment-facing layer is the potential of the sensor to present potential for accidental choking. This is also a challenge of sensors designed to be reusable, whether disposed internally of the absorbent article or externally due to their removable/reusable nature.

It is a goal to overcome the challenges mentioned above. Particularly, one goal of the present disclosure is to locate the sensor in or on an absorbent article, either internally or externally, or on an auxiliary article, such that the potential for creating a choking hazard is greatly reduced. It is also a goal of the invention to size and/or shape the sensor to decrease the potential for creating a choking hazard.

DETAILED DESCRIPTION

Figure 1A:
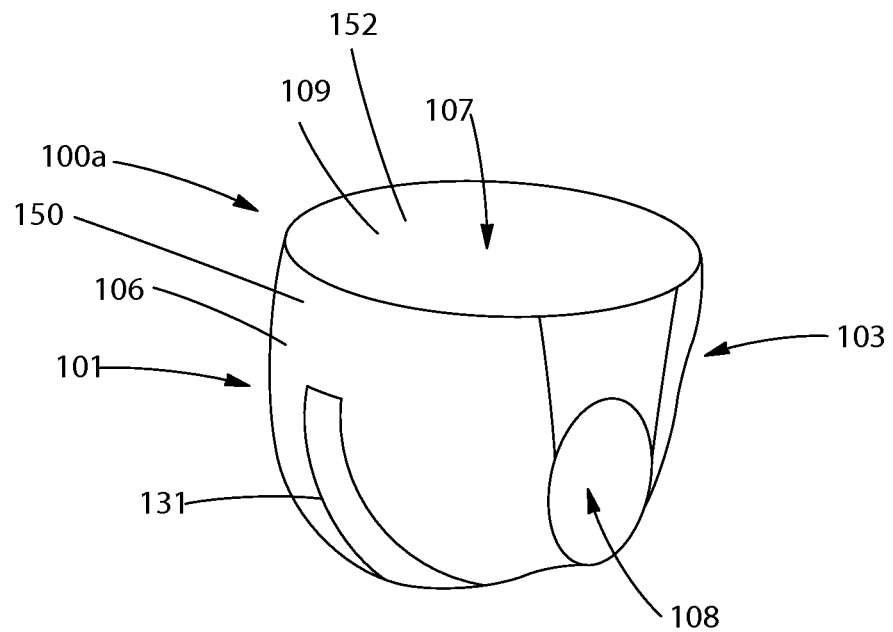
FIG. 1A illustrates a pant-type absorbent article with a sensor in the front, according to embodiments of the present disclosure.

Embodiments of the present disclosure illustrate various absorbent articles comprising various sensors and/or auxiliary articles comprising various sensors that may be used with various absorbent articles to make a sensor system. And, as described above, the sensors of the present disclosure are located on or in an article and/or designed to prevent or reduce the risk of choking.

Absorbent Article

The absorbent article may be one for personal wear, including but not limited to diapers, training pants, feminine hygiene products, incontinence products, medical garments, surgical pads and bandages, other personal care or health care garments, and the like. Various materials and methods for constructing absorbent articles such as diapers and pants are disclosed in U.S. Pub. Nos. 2011-0041999, 2010-0228211, 2008-0208155, and 2009-0312734.

The sensor may be discrete from or integral with the absorbent article. The absorbent article may comprise sensors that can sense various aspects of the absorbent article associated with insults of bodily exudates such as urine and/or BM (e.g., the sensor may sense variations in temperature, humidity, presence of ammonia or urea, various vapor components of the exudates (urine and feces), changes in moisture vapor transmission through the absorbent articles garment-facing layer, changes in translucence of the garment-facing layer, color changes through the garment-facing layer, etc.). Additionally, the sensors my sense components of urine, such as ammonia or urea and/or byproducts resulting from reactions of these components with the absorbent article. The sensor may sense byproducts that are produced when urine mixes with other components of the absorbent article (e.g., adhesives, agm, etc.). The components or byproducts being sensed may be present as vapors that may pass through the garment-facing layer. It may also be desirable to place reactants in the diaper that change state (e.g. color, temperature, etc.) or create a measurable byproduct when mixed with urine. The sensor may also sense changes in pH, pressure, odor, the presence of gas, blood, a chemical marker or a biological marker or combinations thereof.

The sensor may be removably integrated with the absorbent article with hook and loops fasteners, adhesives, thermal bonds, mating fasteners like snaps or buttons, or may be disposed in pockets, recesses or void spaces built into the absorbent article, or combinations thereof. Many of these integration means enable removal of and/or attachment of the sensor from or to the absorbent article. The absorbent article may further comprise graphics for the purpose of properly locating the sensor. The graphics may appear as an outline of the sensor, may symbolize a target, may be a different color than the surrounding area of the article, may state, "Place sensor here," may correspond with instructions from a manual, or may be combination of one or more of these approaches.

Regarding pockets, it may be desirable to form a pocket with or adjacent to the wearer-facing layer or garment-facing layer. In some embodiments, a pocket may be formed by joining an additional material (e.g., a nonwoven strip) to the interior or exterior surface of the garment-facing layer. When joined to the interior surface of the garment facing layer, it may be desirable to position an open edge (to be the pocket opening) of the sheet to be coterminous or adjacent to an edge of the waist opening such that there is no need to make a cut in the garment facing layer for inserting the sensor into the pocket opening.

When joined to the exterior surface of the garment-facing layer, the non-open edges of the sheet may be permanently joined, while an open edge (to be the pocket opening) may be refastenably joined to the garment-facing layer.

FIGS. 1A-2C illustrate acceptable absorbent articles, each with one or more sensors. For clarity, FIGS. 1A-2C do not illustrate all details of the sensors or of the absorbent articles. Each sensor and/or absorbent article in FIGS. 1A-2C can be any embodiment of the present disclosure.

FIG. 1A illustrates an outside perspective view of a front 101 and a side 103 of a pant-type absorbent article 100A formed for wearing. The pant-type absorbent article 100A may include a waist opening 107, a leg opening 108, an exterior surface (garment-facing) 106 formed by a garment-facing layer 150A sometimes referred to as the garment-facing layer, and an interior surface (wearer-facing) 109 formed by a wearer-facing layer 152A sometimes referred to as the wearer-facing layer. The absorbent article 100A may include a longitudinally oriented sensor 131 disposed in the front 101.

The wearer-facing layer 152A may be a layer of one or more materials that forms at least a portion of the inside of the front-fastenable wearable absorbent article and faces a wearer when the absorbent article 100A is worn by the wearer. In FIG. 1A, a portion of the wearer-facing layer 152A is illustrated as broken-away, in order to show the garment-facing layer 150A. A wearer-facing layer is sometimes referred to as a topsheet. The wearer-facing layer 152A is configured to be liquid permeable, such that bodily fluids received by the absorbent article 100A can pass through the wearer-facing layer 152A to the absorbent material 154A. In various embodiments, a wearer-facing layer can include a nonwoven material and/or other materials as long as the materials are liquid permeable over all or part of the wearer-facing layer.

The absorbent material 154A may be disposed subjacent to the wearer-facing layer 152A and superjacent to the garment-facing layer 150A, in at least a portion of the absorbent article 100A. In some embodiments, an absorbent material of an absorbent article is part of a structure referred to as an absorbent core. The absorbent material 154A may be configured to be liquid absorbent, such that the absorbent material 154A can absorb bodily fluids received by the absorbent article 100A. In various embodiments, an absorbent material can include cellulosic fibers (e.g., wood pulp fibers), other natural fibers, synthetic fibers, woven or nonwoven sheets, scrim netting or other stabilizing structures, superabsorbent material, foams, binder materials, adhesives, surfactants, selected hydrophobic materials, pigments, lotions, odor control agents or the like, as well as combinations thereof. The absorbent structure may comprise one or more storage layers and one or more surge management layers. A pair of containment flaps, elasticated leg cuffs, may form a portion of the interior surface of the absorbent assembly for inhibiting the lateral flow of body exudates.

The garment-facing layer 150A may be a layer formed of one or more materials that form at least a portion of an outside of the front-fastenable wearable absorbent article and may face a wearer's garments when the absorbent article 100A is worn by the wearer. A garment-facing layer is sometimes referred to as a backsheet. The garment-facing layer 150A may be configured to be liquid impermeable, such that bodily fluids received by the absorbent article 100A cannot pass through the garment-facing layer 150A. In various embodiments, a garment-facing layer can include a nonporous film, a porous film, a woven material, a nonwoven fibrous material or combinations thereof. The outer cover may also be stretchable, extensible, and in some embodiments it may be elastically extensible or elastomeric. The garment-facing layer 150A may also be vapor permeable and yet liquid impervious.

Throughout the present disclosure, a reference to a pant-type absorbent article can refer to an embodiment that is side-fastenable or to an embodiment without fasteners. A reference to a pant-type absorbent article refers to an article having preformed waist and/or leg openings. Thus, each embodiment of an absorbent article of the present disclosure that is described as pant-type can be configured in any of these ways, as will be understood by one of ordinary skill in the art.

Figure 1B:
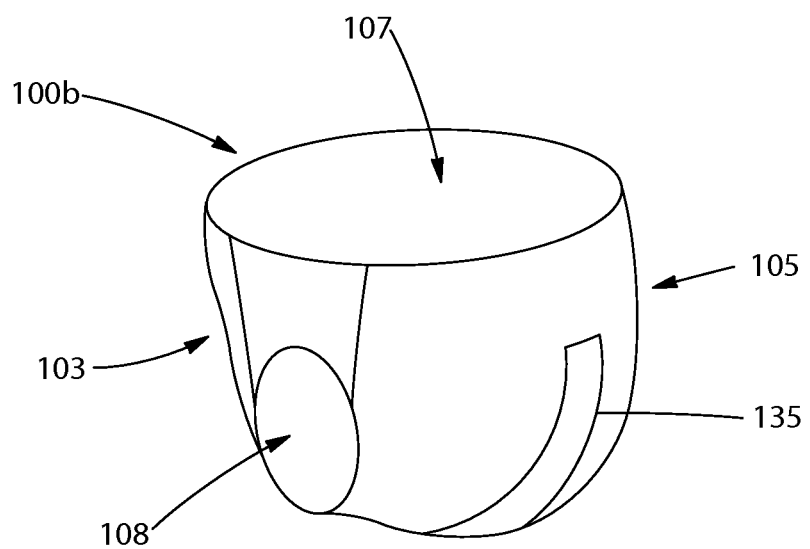
FIG. 1B illustrates a pant-type absorbent article with a sensor in the back, according to embodiments of the present disclosure.

FIG. 1B illustrates an outside perspective view of a side 103 and a back 105 of a pant-type absorbent article 100B formed for wearing. The pant-type absorbent article 100B may include a waist opening 107 and a leg opening 108. Absorbent article 100B may include a longitudinally oriented sensor 135 in the back 105.

Figure 1C:
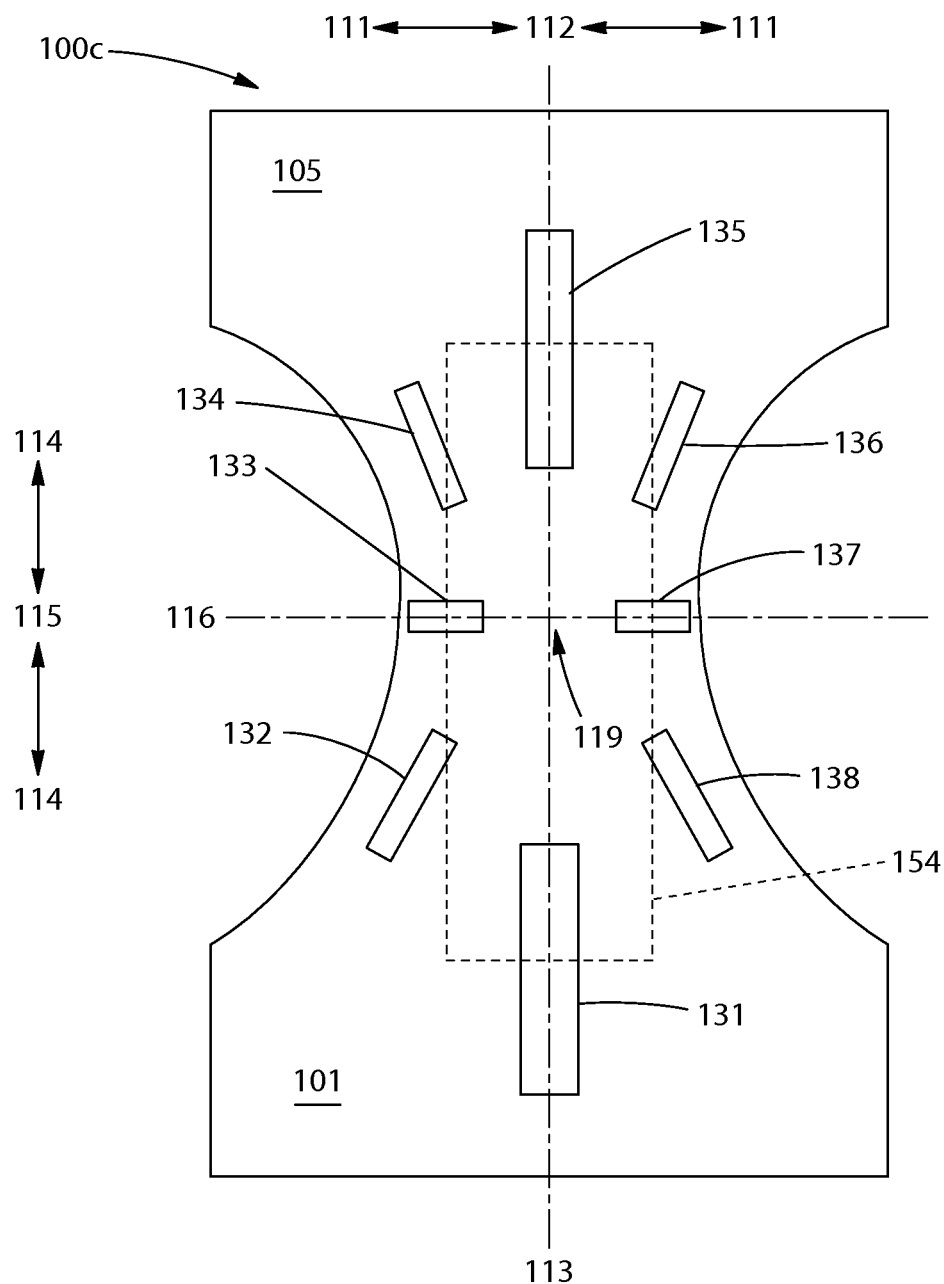
FIG. 1C illustrates a pant-type absorbent article with a plurality of sensors, according to embodiments of the present disclosure.

FIG. 1C illustrates an outside plan view of a pant-type absorbent article 100C laid out flat. The absorbent article 100C may include a front 101 and a back 105, separated by a lateral centerline 116.

In FIG. 1C, a longitudinal centerline 113 and the lateral centerline 116 provide lines of reference for referring to relative locations of the absorbent article 100C. When a first location 112 is nearer to the longitudinal centerline 113 than a second location 111, the first location 112 can be considered laterally inboard to the second location 111. Similarly, the second location 111 can be considered laterally outboard from the first location 112. When a third location 115 is nearer to the lateral centerline 116 than a fourth location 114, the third location 115 can be considered longitudinally inboard to the fourth location 114. Also, the fourth location 114 can be considered longitudinally outboard from the third location 115.

A reference to an inboard location, without a lateral or longitudinal limitation, refers to a location of the absorbent article 100C that is laterally inboard and/or longitudinally inboard to another location. In the same way, a reference to an outboard location, without a lateral or longitudinal limitation, refers to a location of the absorbent article 100C that is laterally outboard and/or longitudinally outboard from another location.

Inboard and outboard can also be understood with reference to a center of an absorbent article. The longitudinal centerline 113 and the lateral centerline 116 cross at a center 119 of the absorbent article 100C. When one location is nearer to the center 119 than another location, the one location can be considered inboard to the other location. The one location can be inboard laterally, or longitudinally, or both laterally and longitudinally. The other location can be considered outboard from the one location. The other location can be outboard laterally, or longitudinally, or both laterally and longitudinally.

FIG. 1C includes arrows indicating relative directions for laterally outboard 111 relative to 112, laterally inboard 112 relative to 111, longitudinally outboard 114 relative to 115, and longitudinally inboard 115 relative to 114, each with respect to the absorbent article 100C. Throughout the present disclosure, a reference to a longitudinal dimension, measurement, line, or direction refers to a dimension, measurement, line, or direction that is substantially or completely parallel to the longitudinal centerline 113 and a reference to a lateral dimension, measurement, line, or direction refers to a dimension, measurement, line, or direction that is substantially or completely parallel to the lateral centerline 116. The terminology for describing relative locations, as discussed above, is used for absorbent articles throughout the present disclosure. This terminology can also be similarly applied to various other absorbent articles, as will be understood by one of ordinary skill in the art.

The absorbent article 100C may include a number of sensors in various exemplary locations and orientations. The absorbent article 100C may include a longitudinally oriented sensor such as sensor 131 and 135, along the longitudinal centerline 113 in the front 101 and/or back 105. The front 101 and/or back 105 may include at least one angled sensor such as sensors 132, 134, 136 and 138 oriented at an angle between the longitudinal centerline 113 and the lateral centerline 116. The absorbent article 100C may include one or more laterally oriented sensors such as sensors 133 and 137 along the lateral centerline 116.

In the absorbent article 100C, the sensors may be oriented substantially radially out from the center 119. However, in addition to the locations and orientations illustrated in FIG. 1C, a sensor of the present disclosure can be disposed in various alternate locations and orientations relative to an absorbent article. As an example, a sensor can be disposed in a pant-type absorbent article at a location relative to a pee point for a wearer of the absorbent article.

Figure 2A:
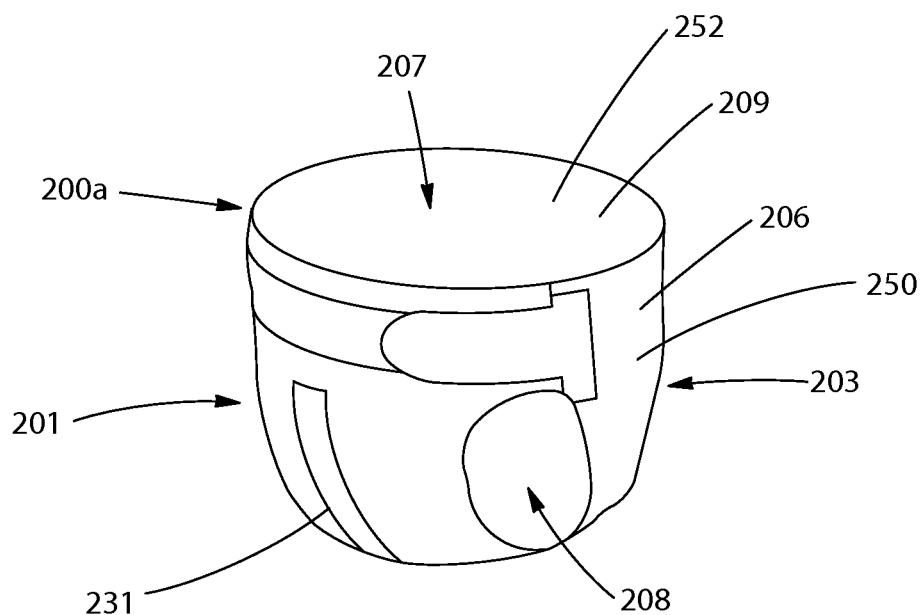
FIG. 2A illustrates a front-fastenable absorbent article with a sensor in the front, according to embodiments of the present disclosure.

FIG. 2A illustrates an outside perspective view of a front 201 and a side 203 of a front-fastenable absorbent article 200A formed for wearing. The front-fastenable absorbent article 200A may include a waist opening 207 and a leg opening 208. The absorbent article 200A may include a longitudinally oriented sensor 231 disposed in the front 201.

While the present disclosure refers to front-fastenable absorbent articles, the present disclosure also contemplates alternate embodiments of absorbent articles wherein the absorbent articles are rear-fastenable. Thus, each embodiment of an absorbent article of the present disclosure that is described as front-fastenable can also be configured to be rear-fastenable.

Figure 2B:
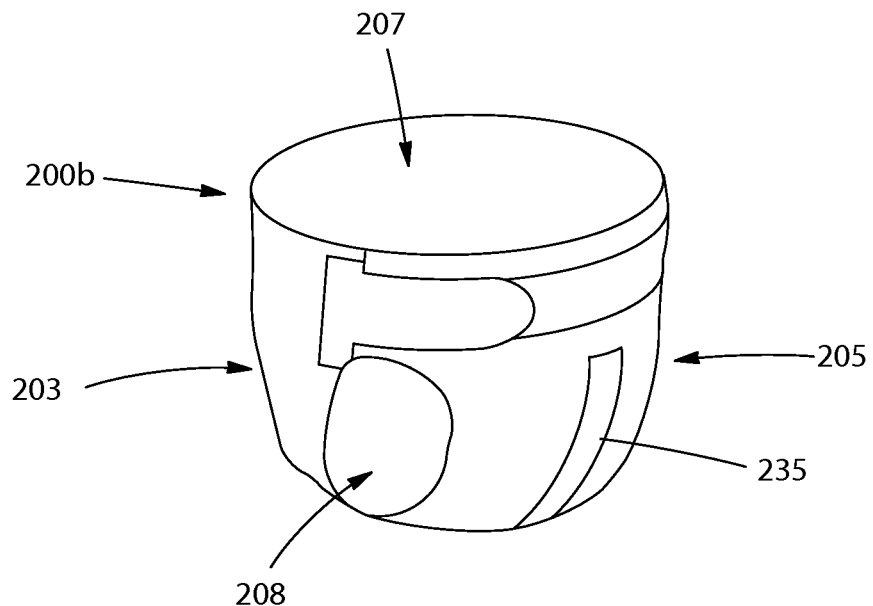
FIG. 2B illustrates a front-fastenable absorbent article with a sensor in the back, according to embodiments of the present disclosure.

FIG. 2B illustrates an outside perspective view of a side 203 and a back 205 of a front-fastenable absorbent article 200B formed for wearing. The front-fastenable absorbent article 200B may include a waist opening 207 and a leg opening 208. The absorbent article 200B may include a longitudinally oriented sensor 235 in the back 205.

Figure 2C:
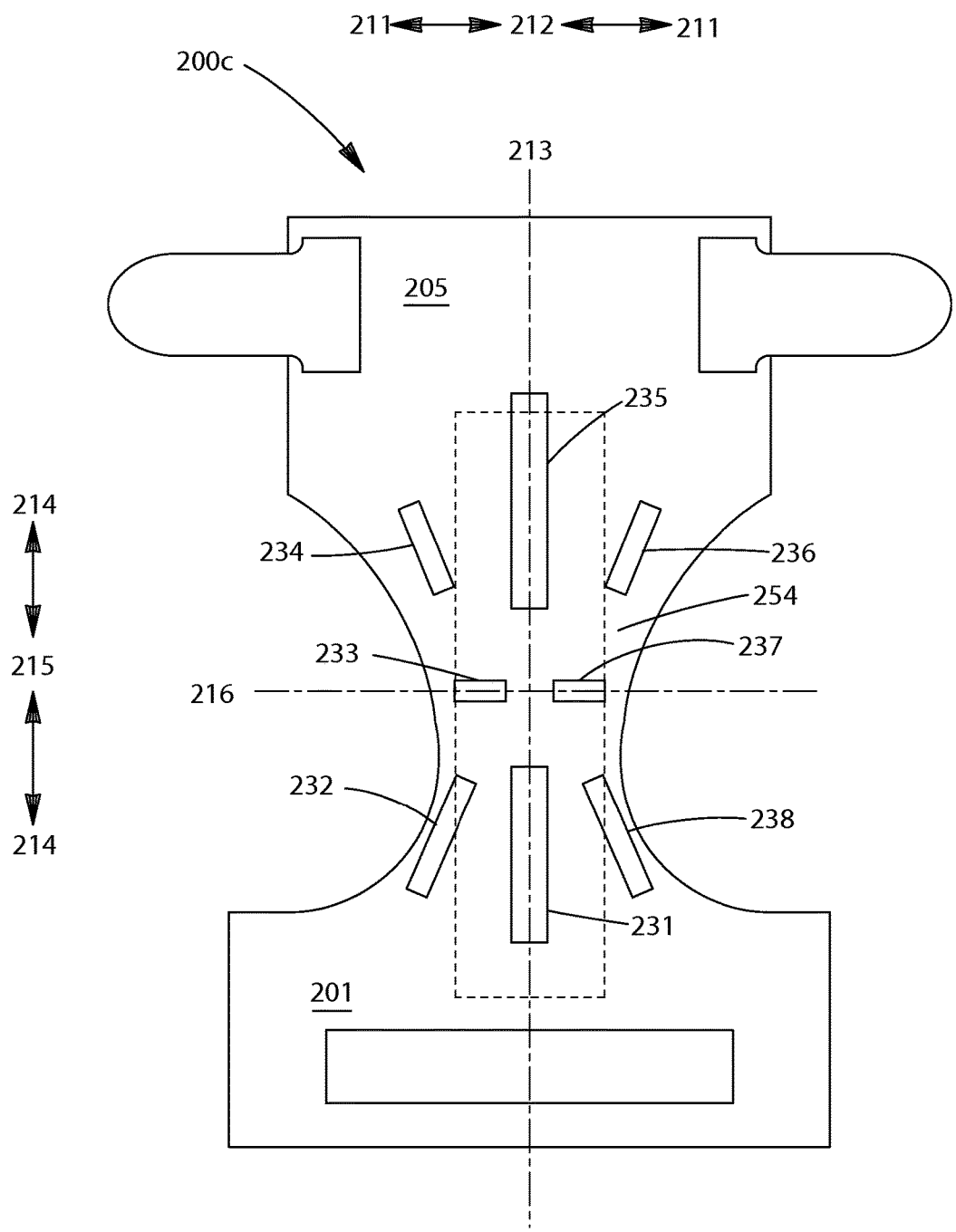
FIG. 2C illustrates a front-fastenable absorbent article with a plurality of sensors, according to embodiments of the present disclosure.

FIG. 2C illustrates an outside plan view of a front-fastenable absorbent article 200C laid out flat. The absorbent article 200C may include a front 201, a back 205, a longitudinal centerline 213, and a lateral centerline 216, an exterior surface 206, and an interior (wearer-facing) surface 209.

The absorbent article 200C may include a number of sensors in various exemplary locations and orientations. The absorbent article 200C may include longitudinally oriented sensors such as sensors 231 and 235, along the longitudinal centerline 213 in the front 201 and/or back 205. The front 201 and/or back 205 may include angled sensors such as sensors 232, 234, 236 and 238 oriented at an angle between the longitudinal centerline 213 and the lateral centerline 216. The absorbent article 200C may include laterally oriented sensors such as sensors 233 and 237 along the lateral centerline 216.

In the absorbent article 200C, the sensors may be oriented substantially radially out from the center 219. However, in addition to the locations and orientations illustrated in FIG. 2C, a sensor of the present disclosure can be disposed in various alternate locations and orientations in an absorbent article. As an example, a sensor can be disposed in a front-fastenable absorbent article at a location relative to a pee point of a wearer of the article.

Figure 3:
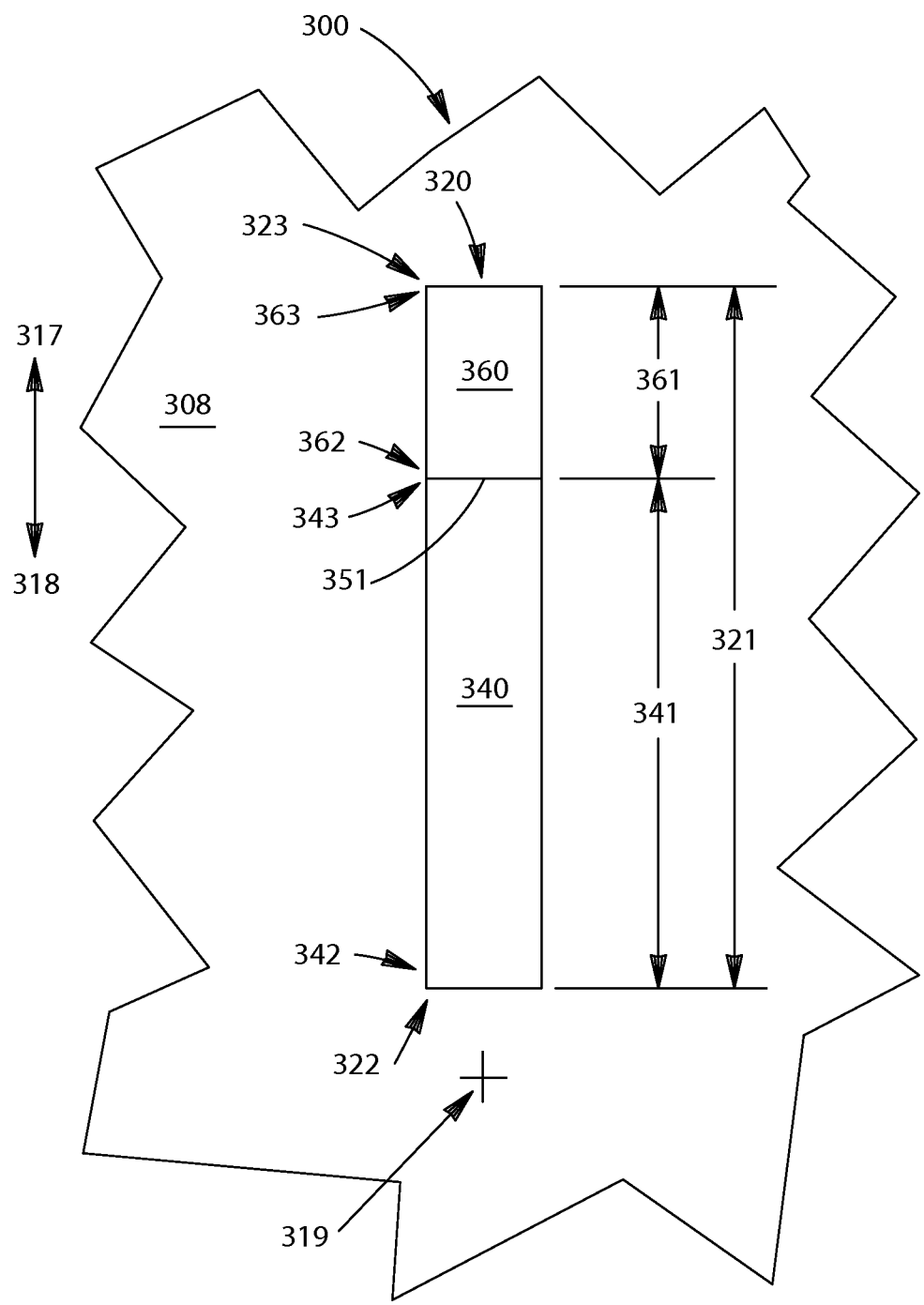
FIG. 3 illustrates a portion of an absorbent article with a sensor having a first sensing area and a second sensing area, according to embodiments of the present disclosure.
Figure 4:
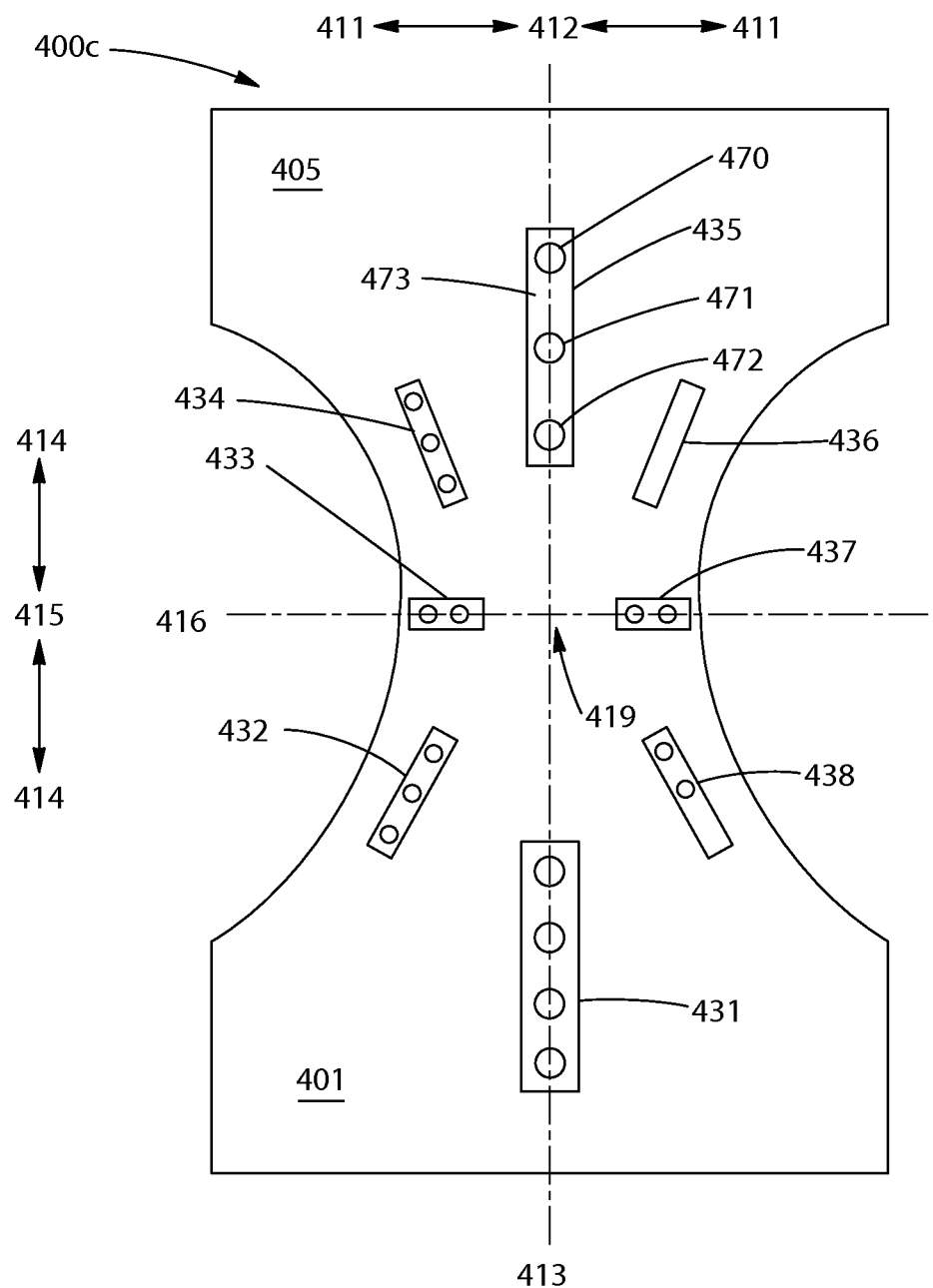
FIG. 4 illustrates a pant-type absorbent article with a plurality of sensors, according to embodiments of the present disclosure.

FIG. 3 illustrates an outside plan view of a portion 308 of an absorbent article 300 laid out flat. In various embodiments, the absorbent article 300 can be an absorbent article, such as a pant-type absorbent article or a front-fastenable absorbent article. In FIG. 3, outside edges of the portion 308 are broken lines, since the portion 308 is illustrated as separate from the rest of the absorbent article 300. For reference, FIG. 3 illustrates a center 319 of the absorbent article 300 and arrows indicating relative directions for outboard 317 and inboard 318 for the absorbent article 300.

The portion 308 of the absorbent article 300 may include a sensor 320. The sensor 320 may be disposed offset from the center 319. In various embodiments, one or more parts of a sensor can be disposed near, at, or overlapping a center of an absorbent article. For example, a single sensing area can extend from a front of an absorbent article, through the center of the absorbent article, to the back of the absorbent article. In such an embodiment, a farthest inboard point along the sensing area can be considered an inboard end of two sensors.

The sensor 320 may include an inboard end 322 and an outboard end 323. The sensor 320 has an overall sensor length 321, measured along the sensor 320 from the inboard end 322 to the outboard end 323. The sensor 320 may have an overall shape that is substantially elongated and substantially rectangular. The sensor 320 may have a substantially uniform width along the entire overall sensor length 321. It may be desirable that the sensor, or a portion of the sensor, has a bending stiffness of less than about 1000 N/m, 600N/m, or 400 N/m (as determined by ASTM D 790-03) to keep it from irritating the wearer. It may alternatively or additionally be desirable to design the sensor, or a portion of the sensor, to have a bending modulus (N/m2) of less than 2.0E+09, 1.0E+08, or 1.0E+06.

In various embodiments a sensor can have an overall shape that is more or less elongated. In some embodiments, all or part of a sensor may be linear, curved, angled, segmented, or any regular or irregular geometric shape (such as a circle, square, rectangle, triangle, trapezoid, octagon, hexagon, star, half circle, a quarter circle, a half oval, a quarter oval, a radial pattern, etc.), a recognizable image (such as a letter, number, word, character, face of an animal, face of a person, etc.), or another recognizable image (such as a plant, a car, etc.), another shape, or combinations of any of these shapes. Also, in various embodiments, an indicator can have varying widths over all or part of its length.

The sensor 320 may include one or more sensing areas for example, a first sensing area 340 and a second sensing area 360. In various embodiments, a sensor can include three or more sensing areas.

The first sensing area 340 may include a first area inboard end 342, a first area outboard end 343, and a first area overall length 341 measured along the first sensing area 340 from the first area inboard end 342 to the first area outboard end 343. The first sensing area 340 may have an overall shape that is substantially elongated and substantially rectangular. The first sensing area 340 may have a substantially uniform width along the entire first area overall length 341. However, in some embodiments, an sensing area can have various shapes and various widths over all or part of its length, as described above in connection with the sensor.

In addition to the first sensing area 340, the sensor 320 may include a second sensing area 360. In the embodiment of FIG. 3, the second sensing area 360 is outboard 317 from the first sensing area 340. The second sensing area 360 may include a second area inboard end 362, a second area outboard end 363, and a second area overall length 361 measured along the second sensing area 360 from the second area inboard end 362 to the second area outboard end 363. In the embodiment of FIG. 3, the second area overall length 361 is less than the first area overall length 341. In some embodiments, a second area overall length can be equal to a first area overall length or greater than a first area overall length.

The second sensing area 360 may have an overall shape that is substantially elongated and substantially rectangular. The second visual fullness sensing area 360 may have a substantially uniform width along the entire second area overall length 361.

Auxiliary Article Structure

One or more sensors may be used with an auxiliary article. The auxiliary article may be a durable, washable, reusable garment designed to fit over an absorbent article. The auxiliary article may be made of various materials, including rayon, nylon, polyester, various polyolefins, spandex, cotton, wool, flax, or combinations thereof.

The auxiliary article may comprise the sensor between two of its layers. A pocket may be formed in or on the inner or outer surface of the auxiliary article. A window may be formed through one or more of the layers of the auxiliary article to provide for better communication between the sensor and the absorbent article.

The sensor may be discrete or integral with the auxiliary article. Integral embodiment may comprise a sensor that can be washed.

The sensor may be removably integrated with the auxiliary article with hook and loops fasteners, adhesives, thermal bonds, mating fasteners like snaps or buttons, or may be disposed in pockets, recesses or void spaces built into the auxiliary article, or combinations thereof. Many of these integration means enable removal of and/or attachment of the sensor from or to the auxiliary article. The auxiliary article may be designed to receive an absorbent article for example an insert. Examples of such auxiliary article chassis that may be desired are disclosed in U.S. Pat. No. 7,670,324 and U.S. Pub. Nos. 2010-0179500, 2010-0179496, 2010-0179501, 2010-0179502, and 2010-0179499.

The auxiliary article may be in the form of a pant-like garment for example children's underwear. The sensors may be adapted to work collaboratively with other forms of children's clothing for example jeans, shorts, overalls, etc. For example, the sensor may be part of an iron-on kit, such that the sensor may be ironed onto a pair of regular underpants or panties. Alternatively, the kit may comprise a patch (or several patches) that can be ironed on or otherwise adhered to the underwear so that the sensor could be removably be attached to the patch. In this embodiment, the sensor could be used from garment to garment.

The sensor disposition and/or patterns disclosed above for the absorbent article can also apply to the auxiliary article.

Throughout the present disclosure, a reference to a pant-type auxiliary article can refer to an embodiment that is side-fastenable or to an embodiment without fasteners. A reference to a pant-type auxiliary article refers to an article having preformed waist and/or leg openings. Thus, each embodiment of an auxiliary article of the present disclosure that is described as pant-type can be configured in any of these ways, as will be understood by one of ordinary skill in the art.

The auxiliary article may also come in the form of a front-fastenable auxiliary article. While the present disclosure refers to front-fastenable auxiliary articles, the present disclosure also contemplates alternate embodiments of absorbent articles, as described herein, wherein the auxiliary articles are rear-fastenable. Thus, each embodiment of an absorbent article of the present disclosure that is described as front-fastenable can also be configured to be rear-fastenable.

The auxiliary article (whether front or rear-fastenable or pant-type) may comprise stretchable materials, extensible materials, elastically extensible materials or combinations thereof disposed at or adjacent the waist and leg openings to provide the extension necessary for application and body conforming fit in use. The front fastening auxiliary article may further comprise and overall stretchable, extensible or elastically extensible layer forming that provides a snug fit of the auxiliary article to the absorbent article.

Sensor Structure

As used in this application, the term "sensor" (e.g., 435) refers not only to the elements (e.g., 470, 471, and 472) responsible for detecting a stimulus and signaling such detection (via impulse), but also includes the housing or carrier layer or substrate (e.g., 473) around such element(s). A "sensor" may include a carrier layer (e.g., 473) with multiple elements (e.g., 470, 471, and 472) capable of detecting one or more stimuli; and, the multiple elements may create multiple locations capable of detecting one or more stimuli. The sensors of the present disclosure may form a part of a sensor system capable of monitoring urine and/or fecal insults. The system that may take on a variety of configurations which are determined by the means in which the presence of urine and/or feces is detected. After detection of urine and/or feces, the system may inform a caregiver and/or a child by generating a notification. The notification may be and auditory signal, an olfactory signal, a tactile signal or a visual signal. It is understood that the system may comprise a device for sending a wireless signal to a remote receiver which may in turn result in an auditory signal, visual signal, tactile signal or other sensory signal and/or combinations thereof.

Manufacturing the sensor independent of the primary disposable absorbent article enables utilization of more expensive components and delivery of more sophisticated sensor technology. For example, internal sensors and/or sensors that are part of the absorbent article may require a built in power source that needs to last through the storage, shelf-life and usage of the absorbent article it is incorporated into. Not to mention, that integrated sensors can introduce significant cost. To offset cost, more simple sensors may be utilized but the functionality and reliability of such cheap sensors would suffer. Stand alone sensors disposed exteriorly of the absorbent article do not have these limitations and could include a means for replacing the power supply or could be rechargeable.

The sensor may be washable and thus created in a water-tight casing or coating capable of withstanding temperatures of greater than about 185° F., or greater than about 200° F.

Various sensors may be used, including inductive, capacitive, ultra sonic, optical, moisture, humidity, chemical, temperature, electromagnetic and combinations thereof.

Sensor Size/Dimension

Whether the sensor is used with an absorbent article (e.g., such that it is joined to the garment-facing layer or wearer-facing layer or placed in a pocket formed by a portion of the absorbent article) or the sensor is used with an auxiliary article (e.g., such that it is joined to an interior or exterior surface or placed in a pocket formed by a portion of the auxiliary article), there may be a desire to design the sensor such that it does not present a potential physical hazard challenge in the event the child were to detach the sensor from the article. A typical physical hazard that such an event could present is choking.

To minimize the choking potential the width of the sensor (which includes its carrier layer) may be designed to be greater than 1.25 inches. If the width of the sensor apparatus is less than 1.25 inches it may be desirable to design it to have a length of greater than 2.25 inches. Other desirable embodiments may be as sensor having a width greater than 1.5 inches and/or a length greater than 3 inches.

Furthermore, it may be desirable that the ends of the sensor (at the narrowest portion) are not curved (convex) because such a curve can open the airway and allow the device to slide further into the windpipe. If a curve is desired, however, it may be desired that it have a radius of curvature greater than 0.25 inches.

An alternative to the width and length dimensions above is to design the sensor with an airway sufficient to enable airflow even if the device gets lodged in the throat of the wearer A contributor to choking may be the wearer's ability to separate the sensor device from the exterior surface of the absorbent or auxiliary article being worn (without regard to whether the sensor is designed to be separable). Removal force is the force to separate two layers of a device or article and/or to separate the device from the article. This separation force can be controlled by limiting the ability of the wearer to grasp the device, for example between their finger tips or alternatively by hooking their finger between the device and the article.

To minimize the fingertip grasping of the device to promote separation the graspable areas around the sensor may be limited to less than 10 mm or less than 5 mm.

To prevent the wearer from getting their fingers between the sensor and article to separate it the bonds, areas of attachment, between the device and article may desirably have a spacing of no more than 20 mm, less than 15 mm or less than 11 mm. A pocket would help minimize both of these factors especially if the pocket is deeper than the device is long and/or the pocket can be closed (e.g., with hooks and loops). Furthermore if the width of the pocket may desirably be less than 20 mm or less than 15 mm to prevent the wearer from accessing the sensor. In addition, if the sensor is disposed at a depth of at least 5 mm, 10 mm, or 15 mm from the end of the pocket the wearer will likely not be able to reach the sensor for inadvertent removal. In such designs it may be beneficial to provide a means for the caregiver to open the pocket adequately to remove the sensor and/or to provide the caregiver with a means for extracting the sensor from the pocket.

Beyond removal force, it may be desirable to have a shear force between the article and the sensor of from about 10 to about 70 N, 20 to about 60 N, or 30 to about 60 N. The pulling force to separate the sensor from the article may be from about 25 to about 500N, or 50 to about 250N.

Thermal Sensor

The sensor of the present disclosure may sense incontinent events by measuring changes associated with the incontinent event. One of the properties of the absorbent article that may be sensed is temperature change of the article associated with introduction of urine or feces associated with an incontinence event. Typical diaper temperatures before urine loading range from about 80 to about 90 degrees Fahrenheit. A urine or fecal insult introduces exudates that are at body temperature, typically 98.6 Fahrenheit, which can be detected through the garment-facing layer of the article. It has been shown that diaper temperature will over time equilibrate into the range of from about 90 to about 92 degrees Fahrenheit after some period of time. Measuring the incontinent event thermally can not only provide an indication of the event itself, but the temperature profile may be used to determine core capacity, and/or size of the insult itself, i.e., amount of urine. The sensor system of the present disclosure may also use the incontinent event as a trigger to review the properties of the wearer and/or the article being monitored before and during the incontinent event. Changes in these properties may show a pattern that can then be used to predict when subsequent incontinent events are likely to occur.

Inductive Sensor

Figure 5A:
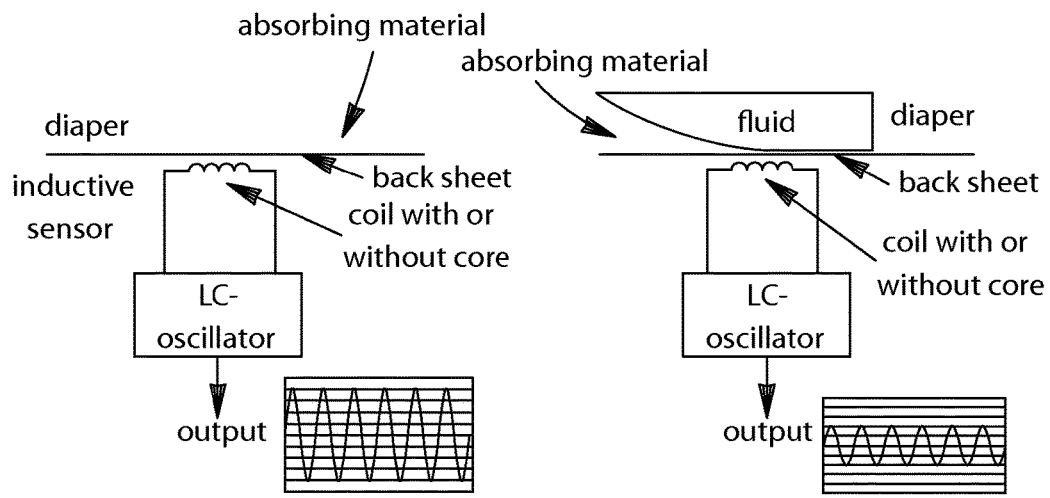
FIGS. 5A-C illustrate an inductive-type sensor, according to embodiments of the present disclosure.
Figure 5B:
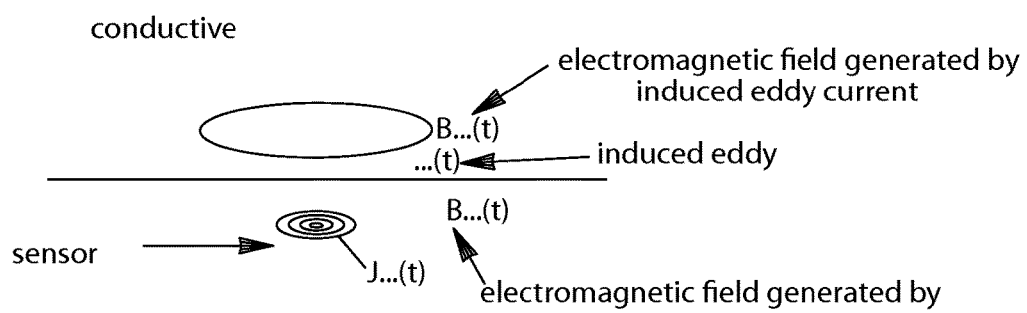
Figure 5C:
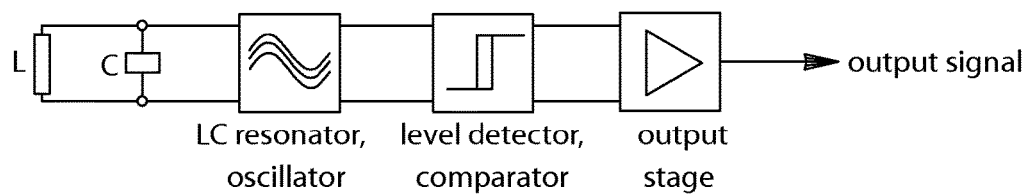
Figure 6A:
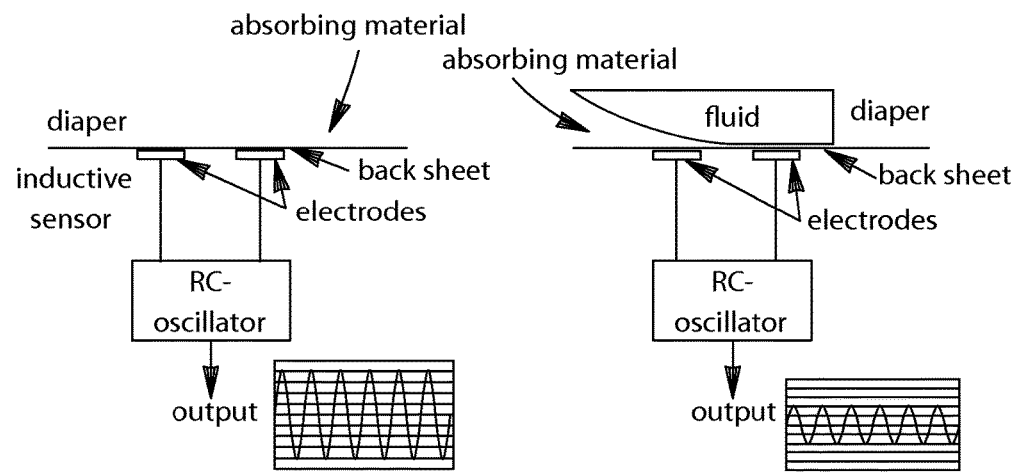
FIGS. 6A-D illustrate a capacitive-type sensor, according to embodiments of the present disclosure.
Figure 6B:
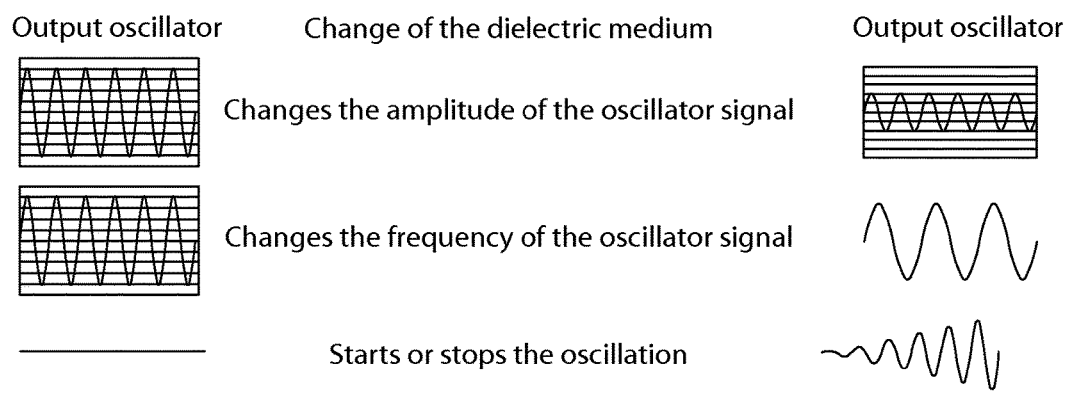
Figure 6C:
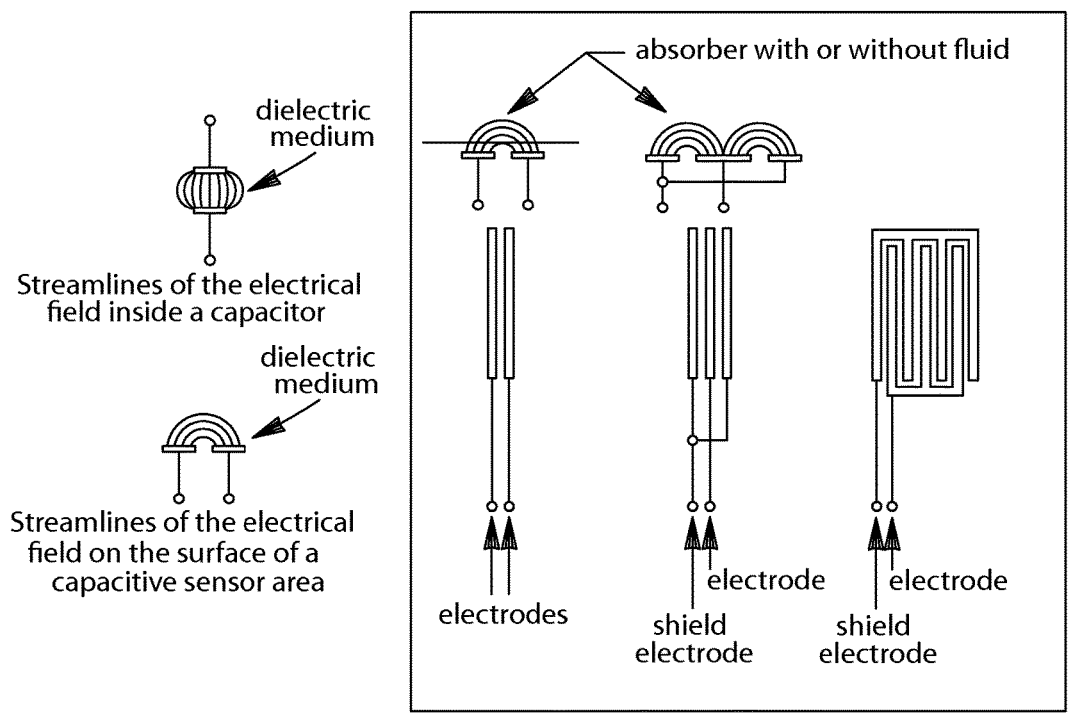
Figure 6D:
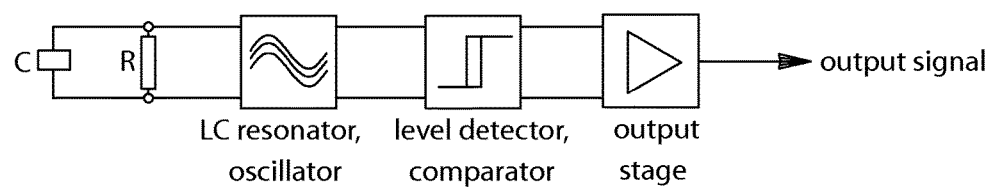

An inductive sensor may be used. Referring generally to FIGS. 5A-C, the inductive sensor may work with a LC-oscillator. This sensor can work by the conductive fluid (urine) damping the oscillating circuit such that the output voltage decreases. Measured data may be gathered from an attached device that detects an change of voltage during urination.

The LC-oscillator may generate a sine wave oscillation at a resonance frequency and an electromagnetic field outside the coil, wherein resonance frequency is $f0=(2\Pi*\sqrt{(LC)})-1$. A conductive material within this field will dampen the oscillating circuit by inducing eddy currents inside the material. Conductive material could be metal, carbon, electrically conductive plastics or electrically conductive fluids like saltwater or urine. The damping of the oscillating circuit decreases the output voltage, this change will be detected and evaluation electronics generate an output signal indicative of the change.

Frequency range of the inductive sensor may be from about 10 kHz to about 100 MHz depending on frequency, coil size and distance. Detection distance may be from about 1 to about 20 mm. Coil dimensions may have a diameter from about 5 mm to about 50 mm. Coil geometry may be a solenoid, copper wire coil with or without a core, or may be a flat, pancake coil made of copper wires or may be printed copper coil on PCB (Printed Circuit Board), or as conductive ink or color printed on paper or plastic foil.

Capacitive Sensor

A capacitive sensor may be used. Referring generally to FIGS. 6A-D, a capacitive sensor may work with an RC-oscillator. The sensor works by fluid changing the dielectric and thus increases the capacity of the electrode arrangement. Dependent on the sensor capacity the frequency and the amplitude of the RC-oscillator changes. Measured data may be gathered from an attached device that detects a change of frequency and amplitude during urination.

The capacitive sensor defines the active sensor area. A change of the dielectric medium decreases or increases the capacity of the electrode arrangement and changes the output signal of the oscillation unit.

Capacitive sensors are able to detect solid materials and fluids, independent of the conductivity of the material. The sensitivity and also the detection distance of the capacitive sensor is related to size of the active sensor area and the material and size of the body that should be detected.

Ultra Sonic Sensor

Figure 7A:
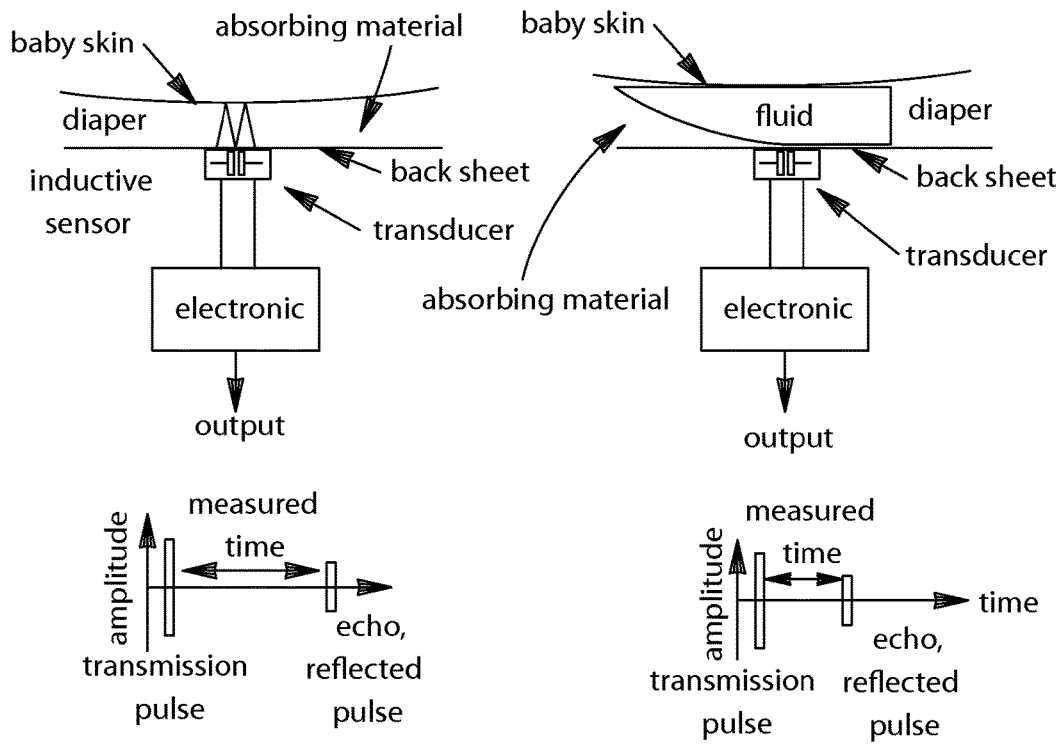
FIGS. 7A-C illustrate an ultrasonic-type sensor, according to embodiments of the present disclosure.
Figure 7B:
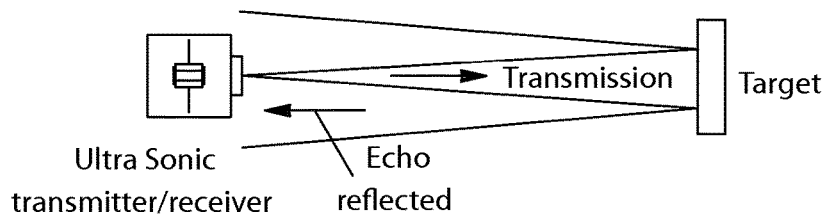
Figure 7B:
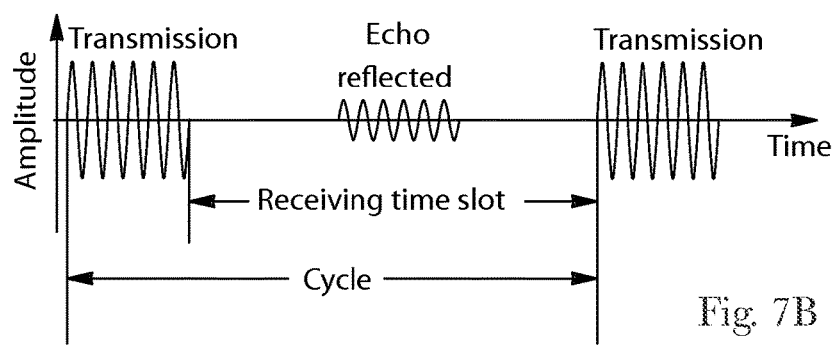
Figure 7C:
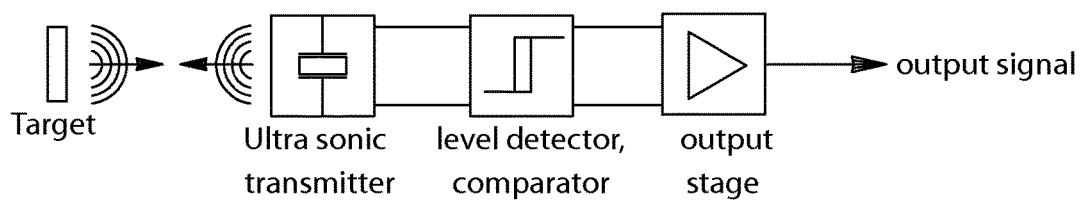

An ultra sonic sensor may be used. Referring generally to FIGS. 7A-C, ultrasonic sensors generate high frequency sound waves in a frequency range from 20 kHz up to 1 GHz.

For distance measurement and object detection they measure the signal run time between transmitted pulse and the echo which is received back by the sensor. Some ultra sonic sensors use separate transmitter and receiver components while others combine both in a single piezoelectric transceiver.

Ultra sonic sensors will work with most of surfaces and also with boundary surfaces between different fluids or gases. The technology is limited by the shapes of surfaces and the density or consistency of the material, but with adapted frequencies and output power is it possible to detect difficult surfaces or materials. Another way to increase the sensor density is to apply variable scan frequencies.

Inside a medium with known density and/or sonic velocity the distance can be calculated as following:

calculation of the distance x based on run time measurement $$v=x/t$$

$$x=v*t$$

t=signal run time
x=distance
v=inside the medium (in air 346 m/sec)
travel distance of the signal=2 times distance to the object:

$$2x=v*t$$

$$x=(v*t)/2$$

In case of a single piezoelectric transducer is used the minimum detectable distance is limited by the recovery time of the piezo. The recovery time depends on piezo size, frequency and on electronics.

The measured time difference between transmitted pulse and received pulse is proportional to the distance to the next boundary surface. The emitted power and the transmitter frequency must be configured to penetrate the dry absorbing material and also the garment-facing layer.

Optical Sensor

An alternative sensor approach of the present disclosure senses incontinent events by measuring optical change of the absorbent article associated with a urine or fecal incontinence event. The sensor may simply measure optical changes as urine or feces contact the garment-facing layer of the absorbent article, e.g., change in color associated with the yellow urine or brown feces. Alternatively, the article may comprise a material placed adjacent the garment-facing layer that reacts with the urine of feces insult to change color and provide the optical indication necessary for sensing. In yet another alternative of an optical sensing system the outer cover may comprise a material that changes in translucency when wet, thereby allowing an inner layer to show through creating the optically measurable change. It should be appreciated that these optical changes are desirably reversible after the insult, for example, once the liquid has been absorbed by the absorbent core. Alternatively, it may be desirable that the optical properties change to a measurable degree with each subsequent incontinent event. Measuring the incontinent event optically can not only provide an indication of the event itself, but the duration of the optical change particularly in a reversible change structure can provide an indication of core capacity, product dryness and/or size of the insult itself, e.g. amount of urine. Sensor systems of the present disclosure may also use the incontinent event as a trigger to review the properties of the wearer and/or the article monitored before and during the incontinent event. Changes in these properties may show a pattern that can then be used to predict when subsequent incontinent events are likely.

In an alternative embodiment, a simple absorbent sheet may become darker when liquid is introduced and as liquid is absorbed back into the absorbent core the simple absorbent sheet may become lighter in color. As stated above, it is preferred that the optical changes are either cyclic in nature, i.e., on and off or are progressive in nature, i.e. changing from one level of intensity to another with each loading. These approaches, cyclic and progressive will enable to sensors to distinguish when a loading has occurred and provide reliable indication.

Chemicals and Properties Sensed

In yet another alternative embodiment, sensors of the present disclosure monitor incontinent events by measuring changes associated with an incontinent event. One of the properties of the absorbent article that may be monitored is transmission of a specific gas or vapor through the article outer cover. The creation of the gas or vapor may be associated with a urine and/or fecal incontinence event. Microporous, breathable outer covers have the ability to pass gases and/or vapors through the pores of the outer cover itself. The monitoring involves one or more reactants that create or generate a gas or vapor when contacted by urine and/or feces. It should be appreciated that the selective gas and/or vapor transmission through the outer cover is desirably cyclic, i.e., lower once the liquid has been absorbed and high when free liquid is present. The magnitude of the cyclic nature of the reactant needs only be sufficient for reliable sensing of the event. Measuring the incontinent event via moisture vapor transmission can not only provide an indication of the event itself, but the moisture vapor transmission profile or threshold values may be used to determine core capacity, product dryness and/or size of the insult itself, e.g., amount of urine. Further, the incontinent event may act as a trigger to review the properties of the wearer and/or the article being monitored before and during the incontinent event. Changes in these properties may show patterns which can then be used to predict when subsequent incontinent events are likely.

Communication

There are a number of acceptable orientations for placing sensors in or on the auxiliary article to ensure the desired sensing of the environment within the absorbent article. For instance, an aperture or absorbent free zone may be created in the core of the absorbent article so that fecal waste or urine are more readily disposed against the garment-facing layer and thereby provide a strong enough stimulus (e.g., chemical, visual, etc.) that is detectable by the sensor. For this purpose, use of a substantially air felt free core may be desirable. Examples of acceptable air felt free cores are disclosed in U.S. Pat. Nos. 5,562,646, 7,750,203, 7,744,576 and U.S. Pub. Nos. 2008/0312617A1, 2008/0312619A1, 2004/0097895A1.

Alternatively, the sensor may comprise a mechanical fastener, e.g., a hook-like material that can engage with the outer surface of the product, nonwoven or loop material to hold the sensor in place. In an alternative approach the sensor may comprise a magnet designed to pull the sensor into contact with the external surface of the absorbent article. In such a design the article may comprise a thin piece of magnetically compatible material.

Sensors of the present disclosure may be designed to predict when an incontinent event may happen. For example, in one embodiment, the sensor may monitor a property of an absorbent article while the article is being worn. The sensor may determine a change in the property of the absorbent article wherein the change is indicative of an incontinent event of the wearer. Further, the sensor may predict conditions indicative of a subsequent incontinent event based on the change in a property. The sensor may make predictions by comparing a series of incontinent events and conditions present at, during or before the incontinent events, and by determining patterns in the conditions present at, during or before the incontinent events. Further, the sensor may provide an insult notification to inform a caregiver and/or the wearer of the presence of an insult in the absorbent article.

Moisture Vapor Transmission

In yet another alternative embodiment, the sensors of the present disclosure may sense incontinent events by measuring changes in moisture vapor transmission through the absorbent article garment-facing layer. Microporous, breathable garment-facing layers have the ability to pass moisture vapor through the pores of the layer itself. The rate of transmission is highly dependent on the distance the liquid is from the surface of the microporous material. Typical microporous materials exhibit significantly higher "wet cup" moisture vapor transmission rates (liquid directly on the surface of the material) than "dry cup" moisture vapor transmission rates (high humidity on one side low humidity on the other). Therefore, such microporous materials will have a higher moisture vapor transmission rate during and immediately after the incontinence event, especially for urine and watery feces, than during the remainder of the wearing time, when the diaper is dry or once the absorbent materials have contained all of the free liquid. It may be desirable to use a breathable garment-facing layer for the purpose of measuring WVTR. WVTRs of garment-facing layers of the present disclosure may range from about 500 to about 8,000, from about 1,000 to about 6,000, or from about 2,000 to about 4,000 $g/m^2/24$ hours (as determined by ASTM E96).

The sensor system of the present disclosure may monitor a second property which is indicative of an intake of a substance by the wearer such a liquid, a solid, or a drug. For example this property may be data the wearer or caregiver may enter via a wireless handheld device or computer comprising a keyboard, mouse or touchpad indicating that the wearer has consumed food and/or liquids or has been given a drug. A pattern may show that at a given time after eating and/or drinking an incontinent event may occur.

The sensor system may predict conditions indicative of a subsequent incontinent event a number of ways. The sensor system may compare the changes in the first and the second properties that are being monitored and compare them with known patterns predictive of incontinent events. Alternatively the sensor system may look for individual incontinent events as indicated by the first property and then looked to changes in the second property which preceded the incontinent event. Upon finding an instance of a change in the second property followed by an incontinent event, the sensor system may then compare other incontinent events for a similar cause and effect relationship. Multiple second properties may be compared to find more complex relationships and patterns.

Sustainability

There is a growing desire to utilize more sustainable absorbent articles. It is too costly and too wasteful to incorporate a sensor into each article, and to throw it away with each absorbent article change. Instead of throwing away hundreds or thousands of disposable sensors per wearer, a single external sensor in an auxiliary article may be reused. The sensor may be oriented in a washable, reusable auxiliary article.

Another advantage of using a single sensor outside the absorbent article is that the sensor may be used with any absorbent article, including brand, type (taped, pull-on diapers, training pants, etc.), size (e.g., infant to adult).

Internal sensors and/or sensors that are part of the absorbent article may require a built in power source that needs to last through the storage and shelf-life of the absorbent article it is incorporated into. Sensors that are removable from the absorbent article and/or auxiliary article may be set in a recharging base or may have replaceable batteries. Alternatively, especially for auxiliary articles, a battery that is integral with the article may be recharged via a port in the article capable of receiving a charging wire that may be plugged into an outlet.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sensor system for detecting a property of or within an absorbent article, comprising:

an absorbent article comprising a garment-facing layer of a backsheet and an absorbent assembly, wherein the backsheet comprises a film;

a sensor comprising a detecting portion and a signaling portion;

wherein the sensor comprises an optical sensor;

wherein the entire sensor, including the detecting portion and the signaling portion, is disposed outside of the film of the backsheet and in communication with or through the garment-facing layer of the backsheet;

wherein the sensor is separable from the absorbent article;

wherein a first portion of the sensor has a first dimension and a second dimension, wherein the first dimension is at least 1 inch and the second dimension is at least 2 inches; and wherein the sensor is configured to sense a change in condition;

wherein the signaling portion is configured to send a wireless signal to a remote receiver;

wherein at least a portion of the sensor has a bending stiffness of less than 600 N/m; and wherein the backsheet film comprises a portion having a WVTR from 1,000 to 6,000 g/m$^2$/24 hours; and wherein the sensor is disposed to overlap the portion of the garment facing layer.

2. The sensor system of claim 1, wherein the sensor is attached to the garment-facing layer of the backsheet via a hook-like material.

3. The sensor system of claim 2, wherein the hook-like material engages with a nonwoven outer surface of the garment-facing layer of the backsheet.

4. The sensor system of claim 1, wherein the second dimension is at least 3 inches wide.

5. The sensor system of claim 1, wherein sensor comprises a housing.

6. The sensor system of claim 5, wherein sensor comprises a carrier layer.

7. The sensor system of claim 6, wherein the sensor, carrier layer, or sensor housing comprises a shaped portion comprising a radius of curvature greater than 0.2 inches.

8. The sensor system of claim 6, wherein the sensor, carrier layer, or sensor housing comprises one or more apertures.

9. The sensor system of claim 1, wherein the sensor is attached to the absorbent article via a plurality of attachment sites, wherein the spacing between the attachment sites is less than 15 mm.

10. The sensor system of claim 1, wherein the hook-like material engages with a loop material attached the garment-facing layer of the backsheet.

11. The sensor system of claim 1, wherein sensor comprises a moisture sensor.

12. The sensor system of claim 1, wherein the absorbent article comprises a pocket configured to receive the sensor, wherein the pocket has a length of at least 5 mm greater than the length of the sensor.

13. The sensor system of claim 12, wherein the pocket comprises a closure element.

14. The sensor system of claim 1, wherein the sensor comprises an electromagnetic sensor.

15. A sensor system for detecting a property of or within an absorbent article, comprising:

an absorbent article comprising a garment-facing layer of a backsheet and an absorbent assembly comprising an airfelt-free core, wherein the backsheet comprises a film;

a sensor comprising a detecting portion and a signaling portion;

wherein the entire sensor, including the detecting portion and the signaling portion, is disposed outside of the backsheet film and in communication with or through the garment-facing layer of the backsheet;

wherein at least a portion of the sensor has a bending modulus less than 2.0E+09 N/m2;

wherein the sensor comprises a carrier layer comprising a first and a second element, and wherein the first element and second element are capable of detecting different stimuli;

wherein the signaling portion is configured to send a wireless signal to a remote receiver; and wherein the sensor is configured to sense a change in condition.

16. The sensor system of claim 15, wherein the absorbent article comprises a pocket configured to receive the sensor, wherein the pocket has a width of less than 25 mm.

17. The sensor system of claim 15, wherein the sensor is attached to the garment-facing layer of the backsheet via a hook-like material.

18. The sensor system of claim 15, wherein at least one of the first and second elements is an optical sensor.

19. A sensor system for detecting a property of or within an absorbent article, comprising:

an absorbent article comprising a garment-facing layer of a backsheet and an absorbent assembly, wherein the backsheet comprises a film;

a sensor comprising a detecting portion and a signaling portion;

wherein sensor comprises a moisture sensor;

wherein the entire sensor, including the detecting portion and the signaling portion, is disposed outside of the film of the backsheet and in communication with or through the garment-facing layer of the backsheet;

wherein the sensor is separable from the absorbent article;

wherein a first portion of the sensor has a first dimension and a second dimension, wherein the first dimension is at least 1 inch and the second dimension is at least 2 inches; and wherein the sensor is configured to sense a change in condition;

wherein the signaling portion is configured to send a wireless signal to a remote receiver;

wherein at least a portion of the sensor has a bending stiffness of less than 600 N/m; and wherein the backsheet film comprises a portion having a WVTR from 1,000 to 6,000 g/m$^2$/24 hours; and wherein the sensor is disposed to overlap the portion of the garment facing layer.

20. A sensor system for detecting a property of or within an absorbent article, comprising:

an absorbent article comprising a garment-facing layer of a backsheet and an absorbent assembly, wherein the backsheet comprises a film;

a sensor comprising a detecting portion and a signaling portion;

wherein the sensor comprises an electromagnetic sensor;

wherein the entire sensor, including the detecting portion and the signaling portion, is disposed outside of the film of the backsheet and in communication with or through the garment-facing layer of the backsheet;

wherein the sensor is separable from the absorbent article;
wherein a first portion of the sensor has a first dimension and a second dimension, wherein the first dimension is at least 1 inch and the second dimension is at least 2 inches; and
wherein the sensor is configured to sense a change in condition;
wherein the signaling portion is configured to send a wireless signal to a remote receiver;
wherein at least a portion of the sensor has a bending stiffness of less than 600 N/m; and
wherein the backsheet film comprises a portion having a WVTR from 1,000 to 6,000 g/m$^2$/24 hours; and wherein the sensor is disposed to overlap the portion of the garment facing layer.

* * * * *